United States Patent
Nesa et al.

(10) Patent No.: US 8,822,929 B2
(45) Date of Patent: Sep. 2, 2014

(54) PORTABLE BREATH ANALYSER APPARATUS

(75) Inventors: Guillaume Nesa, Pourrieres (FR); Pierre Combet, Cavaillon (FR)

(73) Assignee: Alcohol Countermeasure Systems (International), Inc. (CA)

( * ) Notice: Subject to any disclaimer, the term of this patent is extended or adjusted under 35 U.S.C. 154(b) by 175 days.

(21) Appl. No.: 13/492,415

(22) Filed: Jun. 8, 2012

(65) Prior Publication Data

US 2013/0074577 A1  Mar. 28, 2013

Related U.S. Application Data

(63) Continuation of application No. 13/146,588, filed as application No. PCT/FR2010/050134 on Jan. 28, 2010, now abandoned.

(30) Foreign Application Priority Data

Jan. 28, 2009  (FR) ...................................... 09 50526

(51) Int. Cl.
| | |
|---|---|
| *G01N 33/497* | (2006.01) |
| *G01J 5/02* | (2006.01) |
| *A61B 5/00* | (2006.01) |
| *A61B 5/08* | (2006.01) |

(52) U.S. Cl.
CPC ............ *G01N 33/497* (2013.01); *A61B 5/4845* (2013.01); *A61B 5/082* (2013.01)
USPC .......... 250/343; 250/339.13; 73/23.3

(58) Field of Classification Search
CPC ................... G01N 2021/0382; G01N 21/3504; G01N 33/497; A61B 5/4845; A61B 5/082
USPC ............... 250/339.13, 343; 600/532
See application file for complete search history.

(56) References Cited

U.S. PATENT DOCUMENTS

| | | | | | |
|---|---|---|---|---|---|
| 2,534,657 | A | * | 12/1950 | Bray .............................. | 250/343 |
| 4,709,150 | A | * | 11/1987 | Burough et al. ........... | 250/338.1 |
| 5,022,406 | A | * | 6/1991 | Tomlinson .................... | 600/532 |
| 5,070,245 | A | * | 12/1991 | Rantala et al. ................ | 250/343 |
| 5,170,064 | A | * | 12/1992 | Howe ............................ | 250/573 |
| 5,747,809 | A | * | 5/1998 | Eckstrom ...................... | 250/345 |
| 5,793,043 | A | * | 8/1998 | Weckstrom et al. ...... | 250/339.13 |

(Continued)

OTHER PUBLICATIONS

"International Recommendation OIML R 126: Evidential Breath Analyzers", International Organization of Legal Metrology, Edition 2012 (E).

*Primary Examiner* — Lisa Caputo
*Assistant Examiner* — Punam Roy
(74) *Attorney, Agent, or Firm* — Dickinson Wright PLLC

(57) ABSTRACT

A portable breath analyzing device to measure the rate of partial gas that is exhaled in the breath fluid. The device includes a rechargeable power supply unit, a device to emit pulsated infrared radiation, an infrared receiver, and a measuring vessel. The emission device includes a heating element; the measuring vessel includes a metallic tube whose interior surface is polished and coated with a deposit that reflects at least the infrared radiation of wavelengths that are between (9 μm, 10 μm) and at each end of the tube, a nozzle comprising a cone-shaped section meant to be placed in the tube axis. The infrared emission device is placed on the longitudinal axis of the tube, at the level of one of the nozzles, and the receiver is placed on the longitudinal axis, at the level of the other nozzle.

8 Claims, 1 Drawing Sheet

(56) References Cited

U.S. PATENT DOCUMENTS

| | | | |
|---|---|---|---|
| 6,599,253 B1* | 7/2003 | Baum et al. | 600/532 |
| 6,943,885 B2* | 9/2005 | Martin | 356/437 |
| 7,132,658 B2* | 11/2006 | Weckstrom et al. | 250/339.13 |
| 7,235,054 B2* | 6/2007 | Eckerbom | 600/532 |
| 7,351,954 B2* | 4/2008 | Zhang et al. | 250/252.1 |
| 7,626,168 B2* | 12/2009 | Fischer et al. | 250/343 |
| 8,143,581 B2* | 3/2012 | Wong | 250/345 |
| 2003/0230716 A1* | 12/2003 | Russell et al. | 250/339.13 |
| 2004/0203169 A1* | 10/2004 | Dreyer et al. | 436/164 |
| 2004/0210152 A1* | 10/2004 | Eckerbom | 600/532 |
| 2007/0081162 A1* | 4/2007 | Roller et al. | 356/437 |
| 2007/0145275 A1* | 6/2007 | Wong | 250/339.13 |
| 2008/0038154 A1* | 2/2008 | Longbottom et al. | 422/84 |
| 2009/0124918 A1* | 5/2009 | Stockmann et al. | 600/532 |
| 2010/0249631 A1* | 9/2010 | Aoki et al. | 600/532 |
| 2011/0270113 A1* | 11/2011 | Heyne et al. | 600/531 |
| 2011/0283770 A1* | 11/2011 | Hok | 73/23.3 |
| 2012/0162655 A1* | 6/2012 | Oida | 356/437 |
| 2012/0242980 A1* | 9/2012 | Russell | 356/51 |
| 2013/0175107 A1* | 7/2013 | Sultan et al. | 180/272 |

* cited by examiner

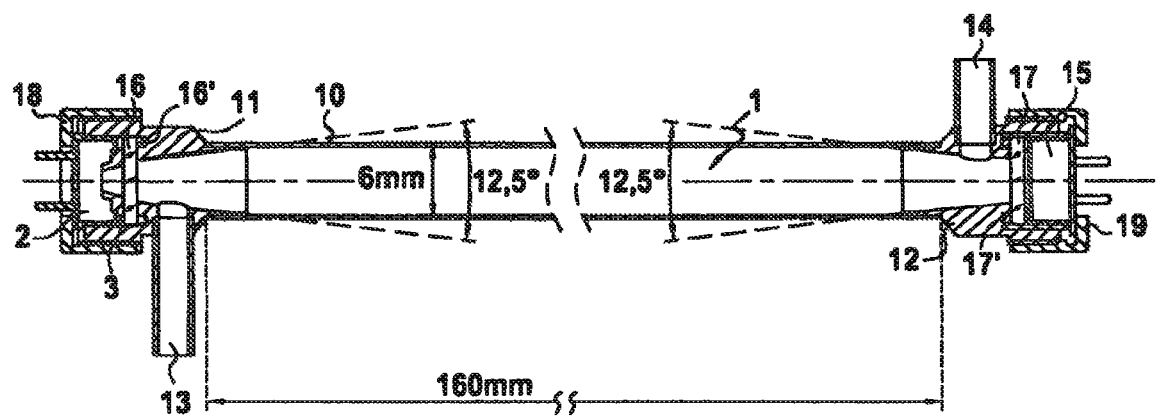

PORTABLE BREATH ANALYSER APPARATUS

INVENTION BACKGROUND

This Invention relates to the general field of portable breath analyzing devices.

More specifically, the Invention is centered on a portable breath analyzing device using emission of a pulsated infrared radiation.

Such portable breath analyzing devices generally include a rechargeable power supply unit, a device to emit the pulsated infrared radiation, an infrared receiver, and a measuring vessel, in which the fluid circulates.

At present, there are many sorts of breath analyzing devices. Most are not portable, and are either based on the use of infrared emission, or on other measuring principles.

However, there are portable breath analyzing devices, but none of the known devices use infrared emission.

It is here noted that a portable breath analyzing device is defined by its accuracy, and the reproducibility of its measurements. Thus, the OIML R126 International Standard defines a breath analyser as having a maximum possible error, positive or negative, of 0.007 mg/L for any concentration below 0.400 mg/L, a maximum possible error, positive or negative, of 1.75% of the measured concentration for any concentration greater or equal to 0.400 mg/L and below or equal to 2.000 mg/L, and a maximum permissible error, positive or negative, of 6% of the measured concentration for any concentration over 2.000 mg/L.

The use of an infrared radiation is not contemplated in portable devices, since one considers that optical paths of lengths over the admitted size for portable devices are necessary.

PURPOSE AND SUMMARY OF THE INVENTION

Thus, this Invention's main goal is to eliminate prejudices and limitations resulting from to known devices, by offering a portable breath analyzing device in which the emission device includes a heating element, whose power is between 60 mW and 130 mW; the measuring vessel includes a metallic tube with an interior diameter between 5 and 12 mm, with a length between 140 mm and 220 mm and whose interior surface is polished and coated with a deposit that reflects at least the infrared radiation of wavelengths that are between ($9\mu$, $10\mu$) and at each end of the tube, a nozzle comprising a cone-shaped section intended to be placed in the tube axis, and whose opening angle is between 8° and 30°. Per the Invention, the infrared emission device is placed on the longitudinal axis of the tube, at the level of one of the nozzles, and the receiver is placed on the longitudinal axis, at the level of the other nozzle. Furthermore, the tube is equipped with heating means, which are able to bring the tube to a temperature above 39° Celsius.

Indeed, the inventors discovered that such dimensions for the measuring vessel and its extremities yielded accuracies per OIML recommendations, with the use of a pulsated infrared source presenting a power between 60 mW and 130 mW, which is compatible with the energy autonomy of the device, while adhering to the general dimensions admitted for portable devices.

The combined use of a nozzle with a cone-shaped section not only allows maximum retrieval of the radiation emitted by the infrared emission devices, but also creation of multiple optical paths, whose length is widely over the tube length. The existence of such optical paths is allowed by the reflective feature of the walls of the tube and of the cone-shaped section in the nozzles.

The multiplication of optical paths allows sufficient quantity of rays to penetrate a sufficient quantity of fluid and thus obtain the typical gaps as defined by OIML recommendations.

According to advantageous features, the heating means include a coiled element on the external surface of the tube.

With such feature, it is possible to maintain the tube at a superior temperature, and thus avoid any form of condensation on the inner walls of the latter during the circulation of the breath fluid which reaches an approximate temperature of 34° Celsius.

Such implementation of heating means allows a minimum energy use to heat the tube.

According to a preferential feature, the interior diameter of the tube is between 6 and 8 mm.

Preferably also, the length of the tube is between 160 and 200 mm.

Advantageously, the angular opening of the nozzles' cone-shaped section Is between 7° and 30°, even more preferably between 8° and 17°.

These features allow optimisation of the optical paths' lengths in the tube, while ensuring sufficient luminous quantity arrives to the end of the tube, opposite the emission device.

Advantageously, the infrared receptor is a pyroelectric sensor.

According to a preferential feature in the Invention, the emission device includes at least one power supply module, capable of providing a pulsated current that is reproducible at a planned pulsating frequency, as well as an emission module made of a substrate on which is placed a layer or a filament of conductive material, serving as a heating element to be powered by the pulsated current; said conductive layer or filament is coated with a layer that is able to transmit heat; on top is placed a thin layer of at least one semi-conductive material.

This preferred feature is an example of the Invention, which is particularly advantageous in a context of device portability, when the conductive layer is powered by pulsated current provided by the power module. Indeed, such an infrared emission device is particularly economical in energy, and this works particularly well with the use of batteries that enable energy autonym for the device.

Known pulsated infrared sources are generally made up of a continuous infrared source, associated with a rotating element, allowing to periodically hide this source, so as to produce a reproducible periodical alternative signal. Such a rotating element is usually called a "chopper". The use of such a rotating element involves implementation of a motor that is capable of providing a constant and totally regular rotation movement, so as to ensure the reproducibility of infrared radiation impulses. The implementation of such a motor involves substantial bulk, as well as the presence of an energy source that is sufficient to operate it, which is not necessarily the case when batteries are used.

With the Invention's preferred feature, implementation of such motor is avoided; which facilitates realization of a portable breath analyzing device according to the Invention.

BRIEF DESCRIPTION OF DESIGNS

This Invention's other features and advantages will be highlighted by the description below, in reference to de attached design which illustrates an example of realization, without any limitation.

FIG. 1 represents essential elements of a portable breath analyzing device per the Invention.

DETAILED DESCRIPTION OF A REALIZATION MODE

FIG. 1 represents an example of realization of the essential parts in a portable breath analyzing device per the invention.

In this device, the measuring vessel is delineated by a tube 10, at which ends are nozzles 11 and 12. On the preferential realisation on FIG. 1, the tube length is equal to 16 mm for a 6 mm diameter.

According to the Invention, the tube is metallic, equipped with an element [not illustrated], which is coiled around tube 10. The presence of this element, which is directly placed on tube 10, helps perform a very quick heating of the tube 10, and therefore of the measuring vessel 1, to allow rapid measuring without substantial wait time for the user.

The nozzle 11 carries an infrared transmitter 2, which is connected to a power supply module [not illustrated] on FIG. 1. Advantageously, the infrared transmitter 2 is equipped with a transmitter cone 3.

The nozzle 12 has a receptive cell 15. The receptive cell 15 is advantageously a pyroelectric sensor. This type of component helps detect thermal radiations in the far spectrum from 3 μm.

Both the transmitter 2 and the receiver 15 are equipped with an optical window, 16 and 17 respectively. These optical windows 16 and 17, associated with O-rings 16' and 17', help set waterproofness between the measuring vessel 1 itself, and the electronic elements for emission 2 and of reception 15 of the infrared radiation. Windows 16 and 17 are advantageously made out of a material that lets the infrared through, for example barium fluoride, which transmission coefficient is over 90%.

Advantageously, the pyroelectric sensor 15 will be equipped with a filter that only lets through the wavelength that corresponds to the alcohol consumption. The optical window 17 in front of the pyroelectric sensor 15 may have a filter that lets through wavelengths of the consumption through OH liaison.

The measurement system per the Invention works in optical monopath. Nozzles 11 and 12 include a tubular entry structure of the sample 13, and a tubular exit structure of the sample 14 respectively. These tubular structures 13 and 14 are advantageously connected to a pumping system, ensuring circulation of the sample blown by the user of the portable breath analyzing device.

Each of the nozzles 11 and 12 presents a cone-shaped structure, whose angular opening is equal to 12.5°. This cone-shaped structure in the nozzles 11 and 12 helps increase the number of optical paths for the infrared radiations that reflect on the inner surface of the tube.

This angular feature of the nozzles' interior 11 and 12 does allow a multiplication of optical paths, while keeping a limited length for the whole measurement device.

The choice of an angular opening for the nozzles 11 and 12 is a compromise between the multiplication of optical paths in the measurement vessel, and the loss in absorption on the optical paths.

Indeed, if the optical paths are too long, it is proven that infrared energy is lost in a significant proportion, which harms the measure accuracy.

However, the path length is important, since it will determine the accuracy for the consumption measurement by gas in the breath fluid.

The cone-shaped structures in the nozzles 11 and 12 as well as the inside of tube 10, show surfaces of a metrological quality.

Preferential dimensions of a measuring vessel per the Invention result from research into a signal to maximize noise ratio, taking into account energy losses connected to the length of the optical paths obtained.

With the structure as described in FIG. 1, 20% of infrared energy circulates without being reflected in the measuring vessel, while 80% of this energy bounces on walls.

Dimensions as defined by the Invention help obtain an optimum between the quantity of partial gas molecules encountered by the infrared radiation, and the quantity of infrared light obtained at the end of the path.

Thus, the combination involving the choice of a diameter, the choice of a length of the vessel, and the angular opening for the internal surface of the nozzles, helps obtain a behaviour optimum from the perspective of the measure, regarding a predetermined power of infrared emission.

Also, it is known that the pyroelectric effect is translated by modifications of the natural polarisation of the ferroelectric element in the sensor, which is a crystal. The absorption of thermal radiation also matches a temperature variation, and is translated by the appearance of electrical loads on the surface.

However, at a constant temperature, the distribution of alternating load must be neutralised by free electrons and surface potential, so that no potential difference is measured.

However, should the temperature be rapidly modified, the timing of internal dipoles will change, which is translated by the appearance of a transitory potential difference.

Thus, the infrared irradiation source must not be constant in intensity, so as to generate variations of polarisation and to allow radiation sensing.

The emission of infrared may thus be performed using a continuous infrared source, associated with a rotating element that periodically hides this source, so as to produce a reproducible periodical alternative signal.

However, it was previously mentioned that the use of such a source of pulsated infrared requires considerable energy, which is generally not available in portable devices that operate with batteries.

Also, in the Invention's preferred realisation, the infrared transmitter 2 is composed of an electronic component that emits reproducible impulses in the spectral interval (9 μm, 10 μm) including at least one power supply module that can provide a reproducible pulsated current at a planned pulsation frequency, and an emission module composed of a flat substrate, on which is placed a thin layer of at least one semi-conductive material; the conductive layer is powered with pulsated current from a power module.

The invention claimed is:

1. A device for receiving a breath sample, the device comprising:
    a metallic tube for receiving the breath sample, the metallic tube having an interior diameter between 5 and 12 mm, a length between 140 mm and 220 mm and an interior surface that reflects at least the infrared radiation of wavelengths that are between (9μ, 10μ);
    at each end of the metallic tube a nozzle comprising a cone-shaped section placed in the tube axis, and whose opening angle is between 8° and 30°;
    a device for emitting pulsated radiation, the device being placed on the longitudinal axis of the tube, at the level of one of the nozzles;
    an infrared receiver placed on the longitudinal axis of the tube, at the level of the other nozzle; and a heating element adapted to bring the tube to a temperature above 39° Celsius.

2. A device according to claim 1, wherein the heating element includes a coiled element on the external surface of the tube.

3. A device according to claim 1, wherein the tube has an inner diameter between 6 mm and 8 mm.

4. A device according to claim 1, wherein the tube length is between 160 mm and 200 mm.

5. A device according to claim 1, wherein the angular opening of the cone-shaped sections of the nozzles is between 7° and 30°.

6. A device according to claim 5, wherein the angular opening of the cone-shaped sections of the nozzles is between 8° and 17°.

7. A device according to claim 1 having a pyroelectric sensor as an infrared receptor.

8. A device according to claim 7 having an emission device that includes at least one power supply module, capable of providing a pulsated current that is reproducible at a planned pulsating frequency, as well as an emission module made of a substrate on which is placed a layer or a filament of conductive material, serving as a heating element to be powered by the pulsated current, wherein said conductive layer or filament is coated with a layer that is able to transmit heat; on top is placed a thin layer of at least one semi-conductive material; and the conductive layer is powered by the pulsated current provided by the power supply module.

* * * * *